Oct. 3, 1944. F. J. MILLER Plant Pat. 644
HOP PLANT
Filed Dec. 6, 1943
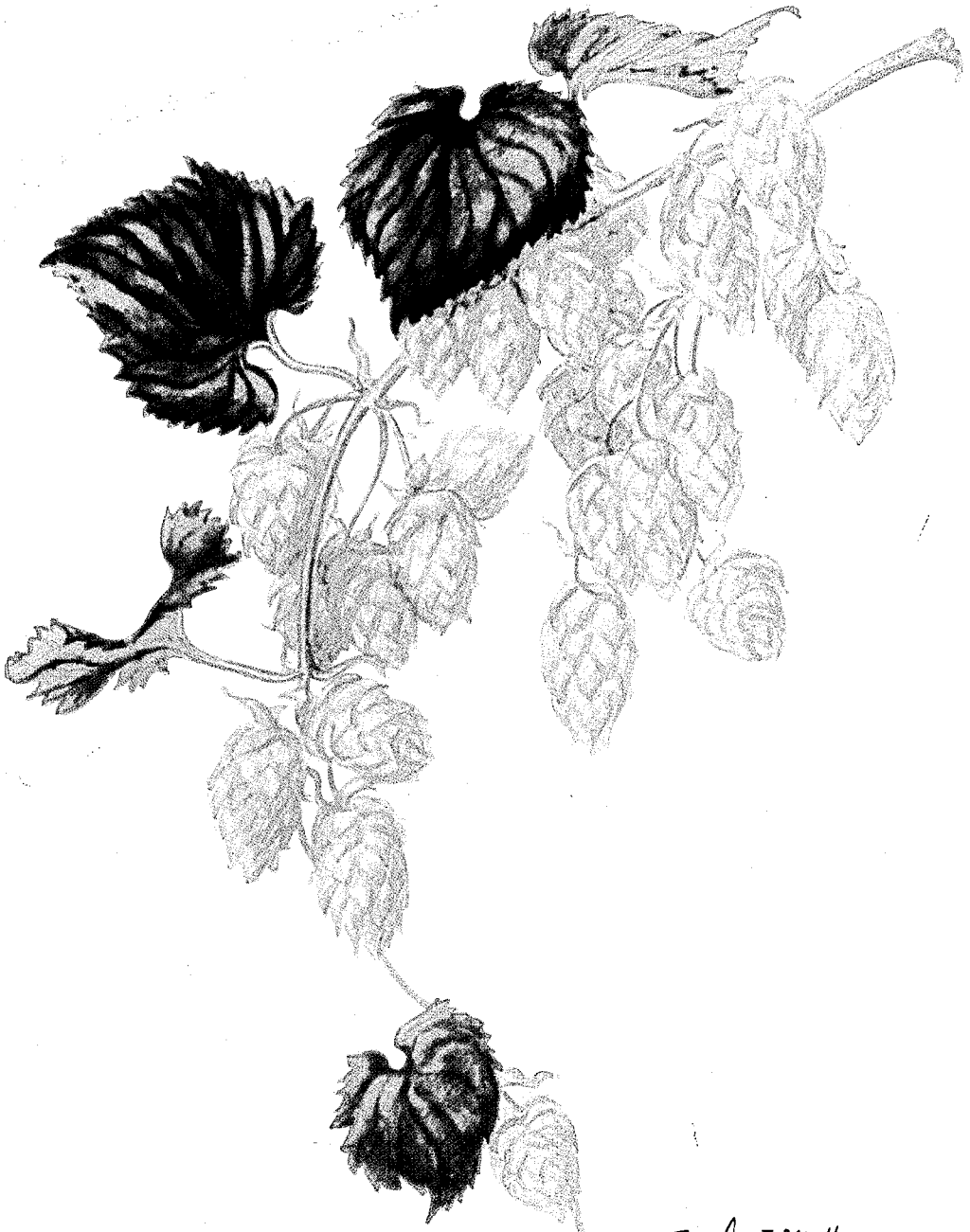
Frank J. Miller, Dec'd
INVENTOR
Phyllis H. McRae &
James L. Larson,
EXECUTRICES,
By Orville M. Kile
PLANT PATENT AGENT Patented Oct. 3, 1944

Plant Pat. 644

UNITED STATES PATENT OFFICE

644

HOP PLANT

Frank J. Miller, deceased, late of Forest Grove, Oreg., by Phyllis Norella McRae and Janness Lola Larson, executrices, Forest Grove, Oreg.

Application December 6, 1943, Serial No. 513,150

1 Claim. (Cl. 47—59)

The present invention relates to definite and extensive improvements in hops of the Bohemian type. There is no known hop which is at all similar. The variety resulted from definite breeding efforts made by Frank J. Miller and originated by crossing a wild English Cluster hop with the Bohemian type hop. The cross took place a number of years ago and has since been developed and asexually reproduced from the root. The characteristics of the variety have proved to be firmly fixed.

The original illustrations which make a part of this application show typical fruits and leaves in approximately their true colors and slightly reduced in size.

This new variety has a great number of outstanding characteristics among which are its healthy growth, small moisture loss, high lupulin content, early ripening and resistance to downy mildew and red spider. A chemical analysis made by the Agricultural Experiment Station at Geneva, N. Y., shows total resins one-half greater in my new variety than in the regular European Bohemian type hops grown in their experimental plots.

Following is a detailed description of this new variety:

Growth: Very healthy but not tall or heavy. Sprouts early in the spring. Is a longer-lived plant and requires less moisture than most varieties. Multiplies rather slowly, due to the fact that there are few lateral branches and side roots.

Root: Very vigorous. Has dark heavy bark. Resistant to usual root diseases of hops, particularly downy mildew.

Vine: Tough and fibrous, having very little sap flow. Small in diameter. Has reddish cast rather than dark green to purple color of other varieties. Surface is smooth rather than barbed, therefore will not catch on one's clothing—an excellent feature at picking time. The vine attains a height of only about 12 feet and has rather short lateral arms. Thus it can be grown on a very low trellis and does not require wire training.

Foliage: Dark green. Most leaves are heart-shaped and smooth-edged rather than the usual cut and lobed leaf of other varieties. However, a few of the largest and oldest leaves are three-lobed.

Fruit: Small, firm, compact, budded berry about one-fourth the size of an ordinary hop which is fluffy in comparison. Develops from a small "burr" rather than from the usual type of blossom. Grows in closely bunched clusters from the ground to the ends of the branches.

*Lupulin content.*—The lupulin content is much higher than average.

*Resin content.*—Very high in total resin content, as compared with the European Bohemian hop as well as other types.

*Flavor and aroma.*—Has an excellent aroma, and no sulphur being required in the drying process makes it possible to keep out certain foreign flavors often present in other hops.

*Dry-out.*—Being a firm, compact berry with low moisture content in the green stage, the loss from dry-out is 60% to 65%, whereas in any other variety it is 75% to 80%.

*Maturity.*—Fruit ripens between the last of July and about August 10th, which is from 15 to 20 days earlier than the regular Bohemian type. This factor removes the variety from competition at harvest time. It also removes the danger of infestation from lice or red spider.

Having thus disclosed the invention, it is claimed:

The new and useful variety of hop plant, substantially as shown and described, characterized as to novelty particularly by its vigorous and healthy root growth; its long life-span; its ability to grow with less moisture than is usual; its tough fibrous smooth vine which grows compactly and relatively low; the development of its fruit from a small "burr" rather than from the usual blossom; its predominately heart-shaped leaf; the early maturity of its fruit; the prolific production of its fruit in compact clusters over the entire vine; its small, compact fruit which contains relatively little moisture but much lupulin and resin, possesses high aroma and excellent flavor, suffers little loss from dry-out, and requires no sulphur in the drying process.

PHYLLIS NORELLA McRAE,
JANNESS LOLA LARSON,
*Executrices of the Last Will and Testament of Frank J. Miller, Deceased.*